United States Patent [19]

Lichtin

[11] 4,427,508
[45] Jan. 24, 1984

[54] LIGHT DRIVEN PHOTOCATALYTIC PROCESS

[75] Inventor: Norman N. Lichtin, Newton Center, Mass.

[73] Assignee: Atlantic Richfield Company, Los Angeles, Calif.

[21] Appl. No.: 374,445

[22] Filed: May 3, 1982

[51] Int. Cl.³ .............................................. B01J 19/12
[52] U.S. Cl. ........................ 204/157.1 R; 204/158 R; 204/162 R
[58] Field of Search ..................... 204/157.1 R, 162 R

[56] References Cited

FOREIGN PATENT DOCUMENTS 55-105625  8/1980  Japan ........................... 204/157.1 R Primary Examiner—Howard S. Williams
Attorney, Agent, or Firm—Roderick W. MacDonald

[57] ABSTRACT

A method for the light driven photocatalytic reduction of carbon dioxide or the bicarbonate ion to one or more compounds which comprises contacting silicon with the carbon dioxide and/or bicarbonate ion in the absence of separate physical electrolyte and electrodes, and conducting said contacting in the presence of light.

20 Claims, No Drawings

LIGHT DRIVEN PHOTOCATALYTIC PROCESS

BACKGROUND OF THE INVENTION

Heretofore, the photocatalytic reduction of carbon dioxide in the presence of water into various organic compounds such as formaldehyde and methanol has been accomplished using various chemical compounds such as titanium dioxide, tungsten trioxide, lead oxide, iron oxide, calcium titanate, silicon carbide, and the like. See "Photoreduction of Carbon Dioxide and Water into Formaldehyde and Methanol on Semiconductor Materials" by Aurian-Blajeni, Halmann and Manassen, Solar Energy, Vol. 25, pp. 165–170, 1980. This photocatalytic process does not employ any physically separate electrodes or special electrolyte as does the classical electrolytic cell or photoelectrochemical cells as will be discussed in greater detail hereinafter. This photocatalytic process merely employs a catalytic material, preferably, dispersed in a carrier liquid for better carbon dioxide contacting purposes. The material to be reduced such as carbon dioxide, is brought into contact with the catalyst using light as a source of the energy of reduction.

Heretofore, such photocatalytic processes have relied on chemical compounds rather than individual elements or metals based on thermodynamic considerations. For example, it was thought that silicon would not work in a photocatalytic context because, based on photoconductor theory, silicon (elemental silicon), when excited by photons would not have sufficient energy to reduce carbon dioxide in a water carrier.

Also heretofore, photoelectrochemical cells which employ two physically separate electrodes combined with a special electrolyte solution have been used to reduce carbon dioxide or the bicarbonate ion to organic compounds such as formaldehyde, methanol, and formic acid. These cells have employed silicon as one of the physically separate electrodes and carbon or the like as the counter electrode. In the operation of these cells at least part of the required energy of reduction is supplied by light energy, including solar radiation. See U.S. Pat. No. 4,219,392, issued Aug. 26, 1980 to Halmann.

BRIEF SUMMARY OF THE INVENTION

Accordingly, it was suprising to discover that silicon, whether semiconductor grade or not, does in fact act as a catalyst in a light driven photocatalytic process for the reduction of carbon dioxide to certain organic compounds.

There is provided, according to this invention, a method for the light driven photocatalytic reduction of carbon dioxide or the bicarbonate ion to at least one organic compound which comprises contacting silicon (elemental silicon) with at least one of carbon dioxide and the bicarbonate ion in the presence of light so that the energy of reduction is essentially supplied by said light.

This process distinguishes clearly over a photoelectrochemical process in that the process of this invention requires no physically separate electrodes or special electrolyte and is unexpected in the photocatalytic context in that, contrary to prior beliefs, it has been found that silicon actually works as a catalyst, and does so even when it is not a semiconductor grade silicon.

Accordingly, it is an object of this invention to provide a new and improved light driven photocatalytic method. It is another object to provide a new and improved method for a light driven photocatalytic reduction of carbon dioxide or the bicarbonate ion to other useful organic compounds. Other aspects, objects and advantages of this invention will be apparent to those skilled in the art from this disclosure and the appended claims.

DETAILED DESCRIPTION OF THE INVENTION

In accordance with this invention, carbon dioxide or the bicarbonate ion or a mixture of both are reduced to at least one compound selected from the group consisting of carbon monoxide, alcohols, aldehydes, hydrocarbons, esters, and carboxylic acids, preferably each having from one to two carbon atoms per molecule, still more preferably carbon monoxide, formaldehyde, methanol, and formic acid. The reduction is accomplished by contacting silicon with one or both of carbon dioxide and the bicarbonate ion and conducting such contacting in the presence of light so that the energy of reduction of the carbon dioxide and/or bicarbonate ion is essentially supplied by said light.

Thus, the useful compounds produced by the method of this invention are obtained without the use of an external electrical bias, special electrodes, or special electrolyte solutions.

The light employed can be sunlight or artificial light or a combination of both and can vary over a wide wavelength range so long as at least part of the incident light is of a wavelength that is absorbed by the silicon employed. The time period for exposure to light can vary widely, there being no upper limit on the time of exposure from an operational point of view. The time limit for each exposure is dictated more by economics.

It has been found that without incident light no measurable reduction takes place, and that with light and no silicon, no measurable reduction takes place, so that the combination of light and silicon along with a reducing agent is necessary.

The silicon employed can be semiconductor grade or not semiconductor grade. If semiconductor grade, the silicon can be either p-silicon, n-silicon, or both (p/n silicon). The semiconductor grade silicon used in this invention can be single crystal, polycrystalline or amorphous in form. All other forms of silicon are not semiconductor grade, e.g., metallurgical grade silicon, chemical grade silicon, and the like. It has also been found that silicon which is not semiconductor grade is operable in this invention. Thus, a wide range of silicon materials can be employed in this invention.

The silicon is preferably employed in a subdivided form, for example, a powder, in order to expose a larger catalyst contacting surface to the carbon dioxide and/or bicarbonate ion. The extent of subdivision is not critical to the operability of the process, it being well within the skill of the art to determine whether coarse or fine particles or a combination thereof are to be employed in a particular application.

Although the mechanism is not yet understood to a certainty, it is thought that silicon may act as a net reducing agent by itself. However, additional reducing agents, e.g., water, can be employed to enhance the reduction reaction.

The silicon may be employed without the aid of a carrier liquid, but the silicon can be dispersed in a carrier liquid to promote maximum contact between the silicon and the material to be reduced. This carrier liquid is not employed as an electrolyte but is rather a physical suspension and mixing medium for the silicon and carbon dioxide and, sometimes, as in the case of water, as a reducing agent. The carrier helps provide maximum mixing and intimate contact between the materials in the presence of light. The carrier liquid is not critical as to its chemical composition, so long as it is chemically nondeleterious to the silicon, the material to be reduced, and the reduction products. Preferably, the carrier liquid is common water. The water may or may not have one or more chemical salts dissolved therein, but, unlike an electrolyte, the carrier need not have dissolved salts therein to any appreciable extent so far as the operation of this invention is concerned.

Other reducing agents that can be employed are hydrogen sulfide, organic waste materials such as sewage, vegetable matter or animal waste.

The amount of silicon and the amount and kind of any additional reducing agent employed in the process of this invention is not critical and can vary widely depending on economics and the like, the minimum criterion being only that an amount effective to obtain the desired reduction be present.

The silicon can simply be exposed to the material to be reduced or, optionally, can first be heat treated to increase its activity when subsequently exposed to the compound or compounds to be reduced. If the silicon is heat treated prior to contact with the material to be reduced, it is preferably heated at a temperature of from about 20° C. to about 600° C. for at least one hour. The heating can be carried out in air or inert gas or in a vacuum, and is preferably conducted for from about one hour to about forty-eight hours.

In the following examples, the silicon was prepared by crushing to a fine powder under benzene in an agate mortar, the finest silicon particles being removed by washing with water. The fine particles were removed, not for operability purposes, but for convenience of the experiment since a substantial amount of fines cause foaming which interferes with carrying out the experiment but does not impede the operability of the process. The thus crushed and washed silicon was dried and conditioned as indicated in the examples.

In the examples, carbon dioxide was used as the material to be reduced. Purified grade carbon dioxide was deoxygenated by passage through a solution of chromous perchlorate stored over a zinc amalgam.

Deionized tap water was employed as the carrier liquid.

The carbon dioxide was dispersed through a sintered disc into 25 milliliters of water carrying the subdivided silicon dispersed therein. In Examples 1–6, 0.5 grams of silicon were employed, while Examples 7 and 8 use 0.25 grams. Bubbling of the carbon dioxide through this aqueous silicon suspension provided adequate mixing. The carbon dioxide flow rate was 150 cubic centimeters per minute at 1 atmosphere. The aqueous silicon suspension was contained in a pyrex reaction cell and a 150 watt Xenon lamp with quartz lenses was employed approximately 30 centimeters from the pyrex reaction cell to supply the incident light required for operation of the process.

Effluent gas from the reactor was passed through two traps immersed in, respectively, common ice and dry ice or through two traps containing small amounts of water and immersed in common ice.

The contents of the reactor and the traps were analyzed after each run for methanol, formic acid, and formaldehyde. The methanol content was determined by gas chromatography on Poropak Q with helium as a carrier gas, flame ionization detection, and calibrated with external standards. The formic acid analysis was the same as the methanol analysis. Formaldehyde was determined by the standard chromotropic acid method.

EXAMPLE 1

Single crystal p-silicon Czochralski boules (boron doped) were sawed into photovoltaic cell wafers and the waste silicon dust from this sawing was employed as the catalyst in the two runs of the example.

The reaction time and temperature for both runs was approximately 30° C. and six hours.

In the first run, the subdivided silicon was not subjected to any preliminary heat treatment before being employed in the photocatalytic process. The products of this run were methanol, formaldehyde, and formic acid. The rates of production in micromoles per hour were 0.063 for methanol and 0.16 for formaldehyde.

The second run of this example employed the same type of subdivided silicon except that the silicon was subjected to a preliminary heat treatment which comprised heating the silicon at 300° C. for three hours in a vacuum before the silicon was used as a catalyst in the process. In this run methanol, formaldehyde, and formic acid were all formed, the rates of production of methanol and formaldehyde being 0.063 and 0.23, respectively.

EXAMPLE 2

In this example, several runs were made using semiconductor grade silicon obtained by crushing photovoltaic wafers obtained from single crystal Czochralski boules, the wafers having been doped with both phosphorus and boron. The catalyst employed was n-silicon (1–2 ohm cm.). The runs were carried out at about 30° C. for approximately six hours. The various runs and results are set forth in the following table.

TABLE I

| Run | Wt. of Cat. g./cc of $H_2O$ X100 | Conditions of Prep'n of Catalyst T/°C. | hrs. | Medium | Yields of Products $\mu$mole per hr. (avg.) $CH_3OH$ | $CH_2O$ |
|---|---|---|---|---|---|---|
| 1 | 0.4 | 100 | 12 | Air | 0.65[a] | 0.86[a] |
| 2 | 1.0 | 100 | 12 | Air | 1.00[a] | 1.00[a] |
| 3 | 1.0 | 100 | 12 | Air | 1.28[a] | 1.05[a] |
| 4 | 1.0 | 100 | 48 | Air | 0.90[b] | 3.25[b] |
| 5 | 2.0 | 100 | 12 | Air | 1.48[b] | 2.33[b] |
| 6 | 2.0 | 300 | 4 | Vac. | 1.51[b] | 1.30[b] |

[a] Stored in freezer ~24 hrs between end of run and analysis.
[b] Analyzed immediately after run.

This example shows the effect of varying amounts of catalyst on product yields.

EXAMPLE 3

In this example, various runs were made using silicon catalysts with different formation histories.

In runs 1 through 3, p-silicon (1–2 ohm cm.) obtained from ground, doped Czochralski photovoltaic wafers as described in greater detail in Example 2 above, were employed. In runs 4 through 6, silicon catalysts employed in runs 1 through 3 were re-used. In runs 7 and 8, the silicon was obtained from material that was to be used as feed to Czochralski single crystal growing machines. Each run was conducted for approximately six hours at about 30° C. The results of these runs are set forth in the following table:

TABLE II

| Run | Catalyst[a] | Conditions of Pretreatment | | | Yields of Products μmole/hr.[b] | |
|---|---|---|---|---|---|---|
| | | T/°C. | hrs. | Medium | $CH_3OH$ | $CH_2O$ |
| 1 | p-Si (1–2Ω cm) | 100 | 12 | Air | 1.55 | 1.46 |
| 2 | p-Si (1–2Ω cm) | 450 | 6 | Air | 0.49 | 0.63 |
| 3 | p-Si (1–2Ω cm) | 400 | 4 | Vac. | 1.19 | 0.90 |
| 4 | p-Si re-used | rm temp | 24 | Air | 0.03 | not det'd |
| 5 | p-Si re-used | 100 | 12 | Air | 0.29 | 1.06 |
| 6 | p-Si re-used | 400 | 6 | Air | 0.06 | 1.16 |
| 7 | pre-Cz Si | 100 | 12 | Air | 1.32 | 0.89 |
| 8 | pre-Cz Si | 400 | 4 | Air | 0.64 | 0.15 |

[a]1 g./100 cc of water
[b]Products stored in freezer 24–48 hrs. before analysis.

EXAMPLE 4

In this example n-silicon and p-silicon, both 1–2 ohm cm., were obtained from crushing boron and phosphorus doped single crystal Czochralski wafers. Each type of silicon was subjected to heat treatment at 650° C. prior to use as a catalyst in the process of this invention. Results were that essentially no methanol was formed although some formaldehyde was produced. In both runs of this experiment, the silicon catalyst was heated to 650° C. for four hours in air before being used as a catalyst in the process of this invention for six hours at 30° C. The products were analyzed immediately after each run. For the n-silicon only a trace of methanol was found, whereas for the p-silicon, no methanol was found. For the n-silicon the yield of formaldehyde in micromoles per hour was 0.15 and for p-silicon was 0.06.

This example shows that it is preferable to keep the thermal pretreatment below 650° C., although the process is not rendered completely inoperable at this elevated temperature.

EXAMPLE 5

Various types of silicon catalyst were employed in additional runs, each run producing varying amounts of methanol and formaldehyde. In runs 1 and 6 minor amounts of methane were detected by gas chromatography on Poropak Q at 30° C. Each run was conducted for about six hours at 30° C. The additional details of these runs and the results thereof are set forth in the following table:

TABLE III

| Run | Catalyst[a] | Yields of Products μ mole/hr[b] | |
|---|---|---|---|
| | | $CH_3OH$ | $CH_2O$ |
| 1 | p-Si (1–2Ω cm) | 1.05 | 1.71[c] |
| 2 | p-Si (9–2Ω cm) | 2.70 | 1.28 |
| 3 | n-Si (.15–.2Ω cm) | 1.29 | 1.00 |
| 4 | n-Si (1–2Ω cm) | 1.00 | 1.26 |
| 5 | n-Si (9–10Ω cm) | 0.70 | 1.58 |
| 6 | Si from solar cell blank[e] | 1.00 | 1.18[c] |
| 7 | Si sweepings - 1[f] | 1.19 | 1.02[d] |
| 8 | Si sweepings - 2[f] | 0.29 | 1.96 |

[a]1 g. catalyst/100 cc of $H_2O$. Preconditioned at 100° C. in air for 12 hrs.
[b]Analyzed immediately after run except for[d].
[c]Trace of $CH_4$ observed.
[d]Stored in freezer for 1–2 days before analysis.
[e]Boron and phosphorus doped
[f]Silicon cuttings from boron doped single crystal Czochralski boule

EXAMPLE 6

This example was made with varying runs using different types of silicon and different wavelengths of incident light to give some indication of the effect of wavelength range on product yield. The runs were conducted for approximately six hours at about 30° C.

The various catalysts used, wavelength range used, and product yield are set forth in the following table:

TABLE IV

| Run | Catalyst[a] | Wavelength-Range | Yields of Products[b] μmole/hr | |
|---|---|---|---|---|
| | | | $CH_3OH$ | $CH_2O$ |
| 1 | p-Si (1–2Ω cm) | White | 1.05 | 1.71 |
| 2 | p-Si (1–2Ω cm) | above 300 nm | 1.00 | 1.00 |
| 3 | p-Si (1–2Ω cm) | 350–550 nm | 0.30 | 0.63 |
| 4 | p-Si (1–2Ω cm) | 350–550 nm | 0.23 | 0.69 |
| 5 | p-Si (1–2Ω cm) | above 700 nm | 0.11 | 0.53 |
| 6 | n-Si (1–2Ω cm) | White | 1.00 | 1.26 |
| 7 | n-Si (1–2Ω cm) | above 300 nm | 0.87 | (not done) |
| 8 | n-Si (1–2Ω cm) | 350–550 nm | 0.33 | 0.68 |
| 9 | n-Si (1–2Ω cm) | above 700 nm | 0.19 | 0.60 |
| 10 | Si from solar cell blank[c] | White | 1.00 | 1.18 |
| 11 | Si from solar cell blank[c] | 350–550 nm | 0.51 | 1.09 |

[a]1 g. of cat./100 cc of $H_2O$; cat. preconditioned at 100° C. for 12 hrs. in air.
[b]All analyses immediately after run.
[c]Boron and phosphorus doped singled crystal

EXAMPLE 7

This example was run with two different types of silicon which is not semiconductor grade, i.e., chemical grade silicon as purchased from a chemical supplier, and metallurgical grade silicon. In each run, 0.25 grams of silicon was employed and 25 milliliters of water with the silicon being preconditioned by heating under Argon for 12 hours at 100° C. Using standard sieve analysis techniques, the particle size range of the silicon employed in both runs was in the range of 75 to 150 micrometers. The results are set forth in the following table:

TABLE V

| Run | Catalyst | Yields of Products[a] μ mole/hr | |
|---|---|---|---|
| | | $CH_3OH$ | $CH_2O$ |
| 1 | Chemical Grade Silicon (Fisher) | 1.22 | 1.27 |
| 2 | Metallurgical Grade Silicon[b] | 1.18 | 1.17 |

[a]Six hour runs at about 30° C.
[b]A minor amount of carbon monoxide was detected by the NBS indicator method.

EXAMPLE 8

Silicon dioxide in the form of Ottawa sand was employed in the amount of 0.25 grams per 25 milliliters of water after pretreatment by heating 12 hours in Argon at 100° C. After reaction for 6 hours at about 30° C., no methanol or formaldehyde was produced.

Reasonable variations and modifications are possible within the scope of this disclosure without departing from the spirit and scope of this invention.

I claim:

1. A method for the light driven photocatalytic reduction of carbon dioxide or the bicarbonate ion to at least one compound which comprises contacting silicon with a hydrogen containing material and at least one of carbon dioxide and the bicarbonate ion in the absence of separate physical electrolyte and electrodes, and conducting said contacting in the presence of light so that the energy of reduction is essentially supplied by said light.

2. The method according to claim 1 wherein said light is one of artificial light, sunlight, or a combination thereof.

3. The method according to claim 1 wherein said compounds are carbon monoxide, alcohols, aldehydes, hydrocarbons, esters, and carboxylic acids having from 1 to 2 carbon atoms per molecule.

4. The method according to claim 1 wherein said silicon is semiconductor grade silicon.

5. The method according to claim 4 wherein said silicon is p-silicon.

6. The method according to claim 4 wherein said silicon is n-silicon.

7. The method according to claim 1 wherein said silicon is not semiconductor grade silicon.

8. The method according to claim 7 wherein said silicon is metallurgical grade silicon.

9. The method according to claim 1 wherein said hydrogen containing material is water.

10. The method according to claim 9 wherein said silicon is dispersed in liquid water and said carbon dioxide and/or bicarbonate ion is carried to said silicon by said liquid.

11. The method according to claim 1 wherein said silicon is in subdivided form.

12. The method according to claim 11 wherein said silicon is subdivided into powder form.

13. The method according to claim 1 wherein said silicon is heat treated prior to contact with carbon dioxide or bicarbonate ion by heating at a temperature of from about 20° C. to about 600° C. for at least one hour in either air, an inert gas, or a vacuum.

14. The method according to claim 13 wherein said heat treatment is for from about 1 hour to about 48 hours in argon or air.

15. The method according to claim 13 wherein said heat treatment is for from about 1 hour to about 48 hours in a vacuum.

16. The method according to claim 1 wherein said light has a wavelength range such that at least part of said light is absorbed by silicon.

17. The method according to claim 1 wherein said at least one compound is selected from the group consisting of carbon monoxide, methanol, formaldehyde, formic acid, and methane.

18. The method according to claim 1 wherein said silicon is amorphous silicon.

19. The method according to claim 1 wherein said silicon is chemical grade silicon.

20. The method according to claim 1 wherein said hydrogen containing material is hydrogen.

* * * * *